US008758316B2

(12) United States Patent
Mullejans et al.

(10) Patent No.: US 8,758,316 B2
(45) Date of Patent: Jun. 24, 2014

(54) OSTOMY SYSTEM

(75) Inventors: Peter Mullejans, Alsgarde (DK); Michael Hansen, Gilleleje (DK)

(73) Assignee: Coloplast A/S, Humlebaek (DK)

( * ) Notice: Subject to any disclaimer, the term of this patent is extended or adjusted under 35 U.S.C. 154(b) by 1983 days.

(21) Appl. No.: 10/591,452

(22) PCT Filed: Feb. 28, 2005

(86) PCT No.: PCT/DK2005/000138
§ 371 (c)(1),
(2), (4) Date: Jul. 2, 2007

(87) PCT Pub. No.: WO2005/082298
PCT Pub. Date: Sep. 9, 2005

(65) Prior Publication Data
US 2007/0282284 A1    Dec. 6, 2007

(30) Foreign Application Priority Data
Mar. 1, 2004    (DK) .................................. 2004 00351

(51) Int. Cl.
*A61F 5/44*    (2006.01)

(52) U.S. Cl.
USPC ....................................................... 604/333

(58) Field of Classification Search
USPC ....................................................... 604/333
See application file for complete search history.

(56) References Cited

U.S. PATENT DOCUMENTS

| 3,495,592 | A | * | 2/1970 | Herman ........................ 604/336 |
| 4,449,970 | A | | 5/1984 | Bevan et al. |
| 4,826,495 | A | | 5/1989 | Petersen |
| 4,938,750 | A | | 7/1990 | Leise, Jr. |
| 5,013,307 | A | * | 5/1991 | Broida ........................... 604/338 |
| 5,085,652 | A | * | 2/1992 | Johnsen et al. ............... 604/333 |
| 5,167,650 | A | * | 12/1992 | Johnsen et al. ............... 604/332 |
| 5,306,264 | A | | 4/1994 | Ferguson et al. |
| 5,591,447 | A | * | 1/1997 | Jensen ........................... 424/443 |
| 5,643,234 | A | * | 7/1997 | Lesko ............................. 604/333 |
| 5,690,622 | A | | 11/1997 | Smith et al. |
| 6,135,976 | A | | 10/2000 | Tachibana et al. |
| 6,135,986 | A | | 10/2000 | Leisner et al. |
| 7,214,217 | B2 | * | 5/2007 | Pedersen et al. ............... 604/333 |

(Continued)

FOREIGN PATENT DOCUMENTS

| DE | BE850143 | * | 7/1977 | ................ A61F 5/44 |
| DE | 203 08 266 U1 | | 8/2003 | |

(Continued)

*Primary Examiner* — Tatyana Zalukaeva
*Assistant Examiner* — Ginger T Chapman
(74) *Attorney, Agent, or Firm* — Coloplast Corp., Coloplast A/S; Nick Baumann

(57) ABSTRACT

An ostomy system for receiving bodily waste comprises a drainage bag (200) and a filter (100) comprising an open-cell foam (102) for preventing liquid and solid particles from passing from the drainage bag to its surroundings. The foam defines a passageway for releasing flatus gasses from the drainage bag to its surroundings, and at least a portion of the foam is arranged at a folding line defined by the drainage bag during use thereof. The foam may be a open-cell foam (102) embedded in a closed-cell foam (128) in a filter flange 146. A gas permeable hydrophobic membrane (127) may be provided at an outlet of the open-cell foam (102). The surroundings of the drainage bag (200) may be constituted by the interior of an outer bag.

13 Claims, 8 Drawing Sheets

(56) References Cited

U.S. PATENT DOCUMENTS

| | | | |
|---|---|---|---|
| 7,470,263 B2 * | 12/2008 | Strobech | 604/336 |
| 7,819,850 B2 * | 10/2010 | Mullejans et al. | 604/344 |
| 8,105,298 B2 * | 1/2012 | Mullejans et al. | 604/332 |
| 8,298,201 B2 * | 10/2012 | Albrectsen | 604/333 |
| 8,475,420 B2 * | 7/2013 | Hansen et al. | 604/327 |
| 2007/0027434 A1 * | 2/2007 | Pedersen et al. | 604/333 |
| 2011/0137273 A1 * | 6/2011 | Mullejans et al. | 604/355 |

FOREIGN PATENT DOCUMENTS

| | | | | |
|---|---|---|---|---|
| DE | 2030826 | * | 1/2004 | A61F 5/441 |
| DE | 20 2004 000 323 U1 | | 5/2004 | |
| EP | 0 259 184 | | 3/1988 | |
| EP | 0 358 316 A2 | | 3/1990 | |
| EP | 0 607 028 A1 | | 7/1994 | |
| FR | 2 337 545 | | 8/1977 | |
| GB | 2 215 605 A | | 9/1989 | |
| GB | 2348140 | | 9/2000 | |

* cited by examiner

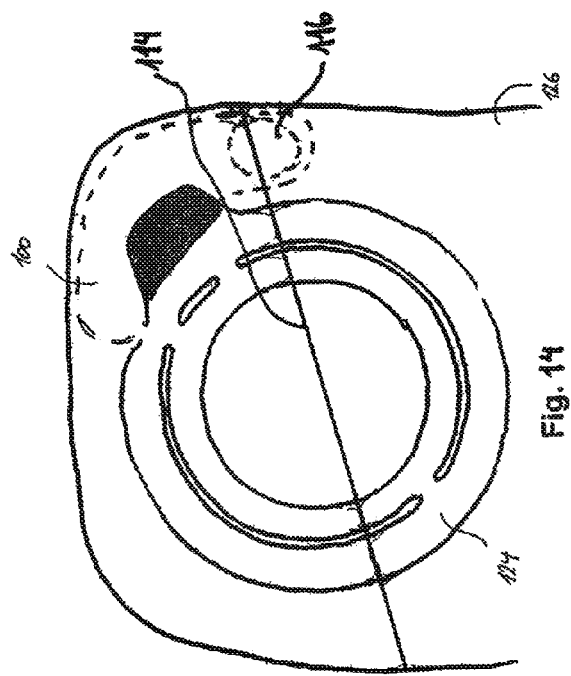
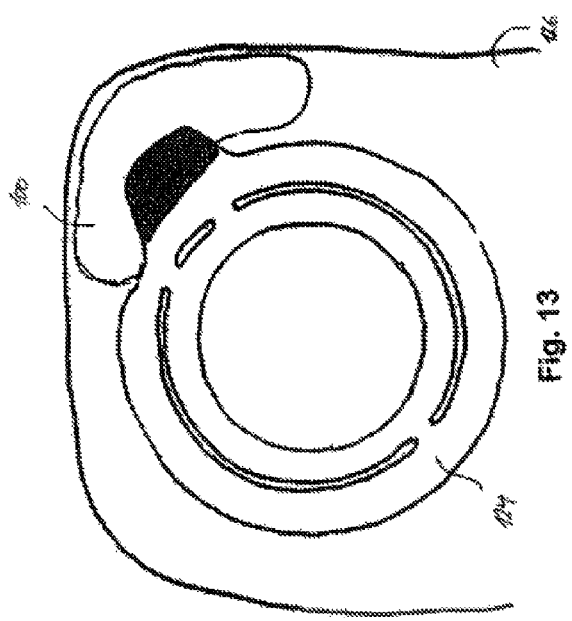

OSTOMY SYSTEM

This is a nationalization of PCT/DK2005/000138 filed 28 Feb. 2005 and published in English.

TECHNICAL FIELD

The present invention relates to ostomy systems for bodily waste. More particularly, the invention concerns an improved filter arrangement of such a system for preventing liquids and solid particles from passing from a drainage bag of the system to the surrounding of the drainage bag.

BACKGROUND OF THE INVENTION

A large number of ostomy bags for receiving bodily waste from colostomy or ileostomy patients have been proposed in the prior art.

European patent application No. 0 607 028 discloses an ostomy bag for holding body waste comprising an envelope formed of flexible plastic sheet material defining a waste collection chamber. The envelope defines a gas outlet proximate a top end portion of the envelope and spaced from a waste inlet opening of the envelope. A deodorizing filter is joined to the envelope in alignment with the gas outlet means for deodorizing gaseous waste material before the gaseous waste exits from the bag through the gas outlet. In the envelope, there is provided means for protecting the deodorizing filter from contact by semi-liquid waste material, and for permitting the flow of gaseous waste, and for obstructing the flow of semi-liquid waste, the protection means comprising a porous protection film preceding the deodorizing filter. The protection means further comprises open cell foam material preceding the porous protection film such that the gaseous waste must pass through the open cell foam material, and through the porous protection film before it passes through the filter. It is thereby sought to provide a multi-stage filter system that prevents semi-liquid waste material from contaminating a deodorizing element but does not inhibit evacuation of gaseous waste through the deodorizing filter.

U.S. Pat. No. 6,135,976 discloses an ostomy appliance comprising a front wall and a rear wall of flexible material, the rear wall having an opening into the bag by which waste material can enter the bag. One of the walls has one or more vents through which gas may escape from the bag. The appliance has a filter covering the vent, the filter comprising an elongated, substantially flat filter body of a porous filter material interposed between gas and liquid impervious walls which are sealed to the body along its longitudinal side edges. Gas inlet and outlet opening are provided in communication with the filter material adjacent to its respective longitudinal end regions. The gas and liquid impervious walls are sealed to the upper end lower surfaces of the filter body. In use, gas flows longitudinally through the filter from the inlet opening to the outlet opening. The inlet opening is covered with a microporous hydrophobic and oleophobic membrane, and the foam material is placed between the front wall and the rear wall and covers the inlet opening of the vent. The appliance of U.S. Pat. No. 6,135,986 thereby shows improved resistance against wetting and blocking of the filter.

It has been found that porous filter arrangements as those suggested in the prior art may tend to clog due to faeces being deposited therein, whereby the drainage bags, including the filters, may have to be replaced at relatively short intervals. It is therefore and object of preferred embodiments of the present invention to provide an ostomy system with a filter arrangement which does not clog as rapidly as the prior art filter arrangements.

SUMMARY OF THE INVENTION

In a first aspect the invention thus provides an ostomy system for receiving bodily waste, comprising:
 a drainage bag;
 at least one filter comprising a foam for preventing liquid and solid particles from passing from the drainage bag to its surroundings, the foam defining a passageway for releasing flatus gasses from the drainage bag to its surroundings; characterised in that
 at least a portion of the foam is arranged at a folding line defined by the drainage bag during use thereof.

As at least a portion of the foam is arranged at the folding line, faeces may be expelled by the foam as pores of the foam are repetitively opened and closed when the drainage bag is folded and unfolded in the area of the foam. Thus, a user of the ostomy system may cause pumping of liquid and solid particles, in particular faeces, out of the foam by folding the bag, such folding occurring naturally when the user seats or lies down, rises after having been seated or having been to bed, walks, bends etc. In the present context, the term folding should be understood as any bending or folding resulting in a compression of the foam. In order to ensure an efficient pumping effect for expelling faeces form the filter, the folding line may intersect the filter at an inlet thereof or at a distance from the filter inlet, for example 5-20 mm from the filter inlet. Expelling of faeces may occur as a consequence of the cross-sectional area of the foam inlet being smaller than the cross-sectional area in the interior foam during folding. When the bag is unfolded, the cross-sectional area of the filter inlet increases, resulting in a pumping or sucking effect which draws faeces deposits from inside the foam towards the inlet.

In an envisaged use of the ostomy system according to the invention, the user may define one more folding lines by folding the bag and/or filter prior to attaching the bag to her or his stoma. For example, instructions may be provided along with the ostomy system, instructing the user to pre-fold the bag prior to attaching it. Alternatively, the bag may be pre-folded, i.e. folded prior to delivery thereof to the user.

In the present context, the term foam should be understood as a porous material, through which flatus gasses may travel, but which serves as at least a partial barrier to liquid and solid particles. Examples of such porous materials are disclosed in prior art documents EP 0 607 028 and U.S. Pat. No. 6,135,986. The foam may have a deodorizing effect which may be achieved by embedding an activated carbon in the foam.

Normally, an ostomy system is not tailored to an individual user, and accordingly the exact position of the folding line may not always be predictable at the stage of designing the ostomy system. Therefore, in one embodiment, the ostomy system comprises a plurality of filters, at least a portion of at least one of the filters being arranged at a folding line defined by the drainage bag during use thereof. Preferably, the plurality of filters are arranged at different positions, so that at least one of the filters is ensured to be in the vicinity of that folding line which is ultimately defined by the user's use of the ostomy system.

The ostomy system preferably comprises a coupling system for securing the bag in relation to a stoma of a patient, the coupling system defining an orifice to enable bodily waste to be received by the drainage bag. In one embodiment, the filter is provided between the coupling system and the drainage bag. In other words, the filter may be provided on that side of the drainage bag, which faces the user (or patient) during use of the ostomy system. Thereby, it may be ensured that forces on the filter resulting from the user's movements are optimally utilised for conferring pumping of liquid and solid particles out of the foam during use of the ostomy system. In one embodiment, the filter is closer to the coupling system than the drainage bag, most preferably such that the filter forms a flange attached to or forming part of the coupling system. It may thereby be ensured that the filter intersects the folding line during use of the ostomy system, as the folding line often intersects the coupling system. The drainage bag may be a biodegradable inner bag surrounded by an outer bag which may be disposed of with household refuse, the filter being thus provided in the inner bag or in the coupling system, so as to prevent liquid and solid particles from passing from the inner bag to the outer bag. The coupling system may serve to secure the inner as well as the outer bag in relation to the patient's stoma.

The filter flange may comprise two sheets of e.g. a gas impermeable material, between which the foam is interposed. The foam is preferably an open-cell foam, i.e. a foam which at least allows flatus gas to pass therethrough. Preferably, the open-cell foam is supported by a closed-cell foam in the filter flange. For example, the open-cell foam may be at least partially embedded in the closed-cell foam in such a way that the filter flange constitutes a ring-shaped or annular body. Thus, it may be ensured that the entire flange is flexible and may bend to define one or more folding lines. In the present context, the term "closed-cell foam" is to be understood as a flexible, preferably hydrophobic material which does not allow flatus gas and liquid to pass therethrough. Near the inlet to the filter, i.e. to the open-cell foam, the open-cell foam preferably constitutes an inwardly facing rim portion of the filter flange, the rim portion preferably extending over a small angle of at most 45°, preferably at most 20°, more preferably at most 10°, such as at most 5°, or between 3° and 15°, preferably between 5° and 10°. From the inlet, the open-cell foam preferably extends in a peripheral direction in the filter flange, interposed between the sheets with closed-cell foam on both sides of the open-cell foam. At the filter outlet, there is preferably provided a hole or perforation in one of the sheets, through which hole the open-cell foam communicates with the surroundings of the drainage bag, e.g. with the interior of an outer bag. At the hole or perforation, there may be provided a barrier to liquid, e.g. a gas permeable hydrophobic membrane.

In case the filter has no deodorizing effect, the outer bag is preferably made from a material which is essentially impermeable to flatus gasses, the outer bag comprising on outlet with a flatus filter for releasing flatus gasses from the outer bag. The flatus filter may be a conventional activated carbon filter.

In one embodiment, the drainage bag is impermeable to flatus gasses, in which case flatus gasses may only escape from the inner bag to its surroundings via the coupling system. The impermeability of the drainage bag may preferably be achieved by a material for the inner bag which is impermeable to flatus gasses. Accordingly, once the drainage bag has been detached from the coupling system, flatus gasses may only escape from the drainage bag through a faeces inlet opening thereof, through which faeces has entered the bag. As the bag is impermeable to flatus gasses, no such gasses escape via the walls of the bag. A user may seal the faeces inlet opening of the bag prior to disposing the bag into a WC bowl, such sealing being, e.g., achieved by the user tying a knot in the inner bag or simply by folding and/or pressing portions of the wall material in the area of the faeces inlet opening. It may hence be achieved that less obnoxious smells diffuse out of the drainage bag during the process of disposing the bag than if the drainage bag is made from a gas permeable material.

As previously mentioned, the foam of the filter may comprise a gas permeable membrane, such as a hydrophobic gas permeable membrane, to provide a further barrier to liquid and solid particles. It will be understood that the actual choice of foam and membrane is a matter of selecting among commercially available products with the required gas permeability and particle/liquid impermeability characteristics. While liquid may normally penetrate into the foam, though not all the way through the foam, provided the foam is sufficiently dense and/or sufficiently thick, the membrane is normally liquid proof. Thus, it is usually desirable to include a membrane in embodiments, in which the coupling system is to withstand large quantities of liquid, or in which the travelling distance through the foam is so small that a risk of liquid penetrating through the foam exists.

As it has become apparent from the above description, the filter may be comprised in a filter flange, whereby the drainage bag is connected to a first surface of the filter flange along an attachment zone, and the coupling system is connected to the filter flange along a contact area. In order to avoid that a displacement force applied to the drainage bag results in detachment of the filter flange from the coupling system, the attachment zone is preferably radially displaced with respect to the contact area. The attachment zone may be at a smaller or larger diameter than the contact area. Conveniently, the drainage is radially closer to an orifice in the coupling system for receiving bodily waste than the contact area between the filter flange and the coupling system. In a preferred embodiment, the coupling system comprises a body flange for attachment to the skin of the patient, and a support flange attached to that side of the body flange, which faces away from the patient's skin. The support flange may thus constitute that part of the coupling system, to which the filter flange is attached. The drainage bag may be enclosed within an outer bag, which may be connected to or supported by the filter flange and/or the support flange.

To ensure that flatus gasses travel a predetermined minimum distance within the foam, the foam may comprise means for forcing the flow of flatus gasses in the barrier along a predetermined flow path. For example, there may be provided a sheet of a plastics material, e.g. PVC, in the foam, the sheet preventing flatus gasses from being conveyed along the shortest, i.e. straight-line route from the inlet to the foam to the outlet thereof. The sheet may e.g. extend along a substantial part of the periphery of the coupling, such as for example along ½ to ⅚ of the periphery. Alternatively, there may be provided a junction, e.g. a welding, at which an outer and an inner flange of the coupling system, between which there is provided the foam, are joined, whereby flatus gasses in the foam are prevented from flowing across the junction.

In case of a biodegradable drainage bag, the material of the bag may be such that the bag essentially maintains its physical integrity upon immersion in water. In the present context, maintenance of the physical integrity of the bag preferably reflects that the bag does not dissolve, i.e. that it retains its structure as one single unbroken entity. It is preferred that the structure of the bag is such that the limpness of the bag remains essentially unaffected when the bag is immersed in water at e.g. at most 30° C., such as at 25° C. The structure of the bag may thus be such that the bag does not loose its physical integrity and/or limpness and/or buoyancy immediately upon immersion in water or shortly thereafter. Preferably, the material of the bag should be such that it essentially maintains its physical integrity and/or limpness and/or buoyancy upon immersion in water at most 30° C., such as 25° C., for at least 10 minutes, preferably for at least 1 hour, such as for at least 6 or at least 12 hours, such as for at least 24 hours, preferably for at least 36 hours, and more preferably for at least 48 hours. Most preferably, the bag maintains its physical integrity at a purifying plant or in a septic tank for at least 1 week, such as for 1-4 weeks. This has several advantages. Firstly, it facilitates a user's handling of a used bag to be flushed away, as the user will not wait for what may appear as an inconveniently long time from placing a used ostomy bag in a WC bowl until the bag has lost its buoyancy, has changed its limpness or lost its physical integrity, at which time the user usually decides to flush away the bag. Once the user has become used to a bag which does not become less buoyant or changes limpness or looses its physical integrity upon immersion in a WC bowl, he or she will not wait at the WC bowl for the bag to sink or disintegrate, and accordingly the user needs to spend less time at the WC bowl. Secondly, as the bag maintains its physical integrity for an extended period of time, it does not dissolve before reaching a purification plant together with the sewage which conveys the bag, and accordingly it may easily be filtered out of the sewage in a water purification process.

In preferred embodiments of the biodegradable drainage bag, the material of the bag comprises a mix of starch, such as maize or potato starch, and polyester, such as synthetic polyester, such as polycaprolactone. It has been found that such a material combines the qualities of being soft, i.e. providing a low level of rustle noise when worn by a user, flexible, and being capable of maintaining its physical integrity upon immersion in water. For example, the material of the bag may comprise 35-55%, such as 40-50% by weight of starch and 35-55%, such as 40-50% by weight of the synthetic polyester. In one embodiment, the material of the bag comprises starch and synthetic polyester in substantially equal ratios. In order to soften the bag and to improve wearing comfort, the bag may comprise 10% or less by weight of a softener, such as glycerol.

In one embodiment, the bag is made from a material of the above composition, the material being essentially insoluble in water. The material may be hygroscopic to such a degree that it absorbs 10-25% by weight of water, such as 15-18%. The water permeability of the material may be between 3000 and 4000 g per $m^2$ per day, and the biodegradability may be such that 10-20 μm of the material thickness is degraded after 2-3 weeks in still water at 25° C. Preferably, the material of the bag fulfils ISO standards for biodegradability.

One suitable material for the bag is the commercially available Mater-Bi NF01U, supplied by Novamont SpA, Novara, Italy.

From the above discussion, it will be appreciated that the present invention also provides a method for expelling faeces from a filter of a drainage bag in an ostomy system, the filter comprising a foam for preventing liquids and solid particles from passing from the drainage bag to its surroundings, the foam further defining a passageway for releasing flatus gasses from the drainage bag to its surroundings and being arranged at a folding line defined by the drainage bag during use thereof, the method comprising expelling faeces from pores of the foam when the foam is folded and unfolded, expelling being caused by repetitive opening and closing of the pores occurring when the drainage bag is folded and unfolded in the area of the foam.

In a further aspect, the invention provides a method of attaching an ostomy system to a user's body, the ostomy system comprising a drainage bag and a filter comprising a foam for preventing liquid and solid particles from passing from the drainage bag to its surroundings, the foam further defining a passageway for releasing flatus gasses from the drainage bag to its surroundings, the method comprising arranging the ostomy system such with respect to the user's body that a folding line defined by the drainage bag during the user's use thereof intersects the filter.

BRIEF DESCRIPTION OF THE DRAWINGS

The invention will now be further described with reference to the drawings, in which:

FIG. 13 shows an example of a different position of the filter.

FIG. 14 shows one embodiment of the ostomy system having a folding line intersecting a filter inlet.

DETAILED DESCRIPTION OF THE DRAWINGS

Figure 3:
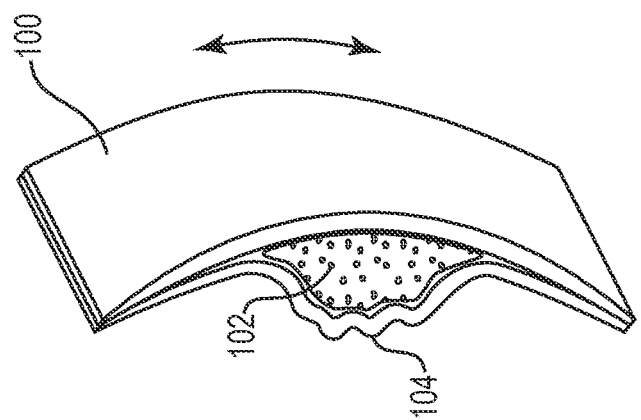
FIGS. 1-3 show three different states of a filter in an ostomy system according to the invention.
Figure 2:
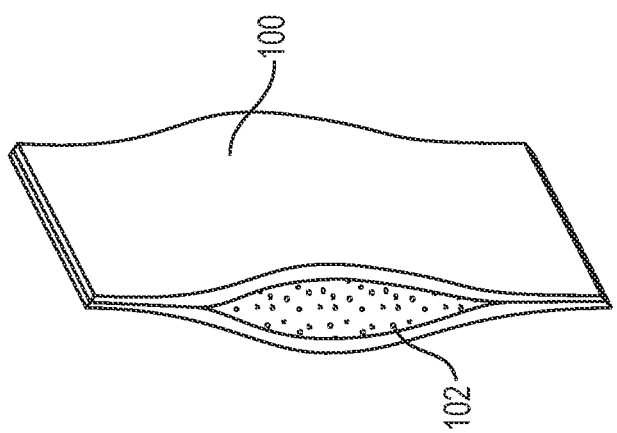
Figure 1:
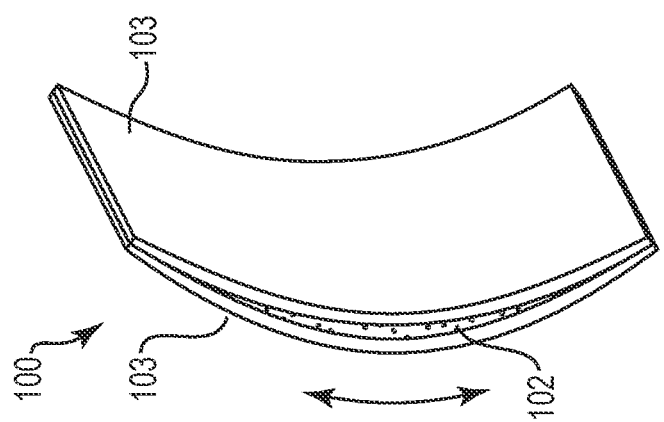

The faeces expelling effect of the filter of the ostomy system according to the present invention is illustrated in FIGS. 1-3, in which the filter 100 comprises a foam 102 interposed between sheets 103. In FIG. 1, the filter is curved, for example as a consequence of the user of the ostomy system bending slightly. As a result, air is pressed out of pores of the foam 102, the pores being thereby more closed than in their open state depicted in FIG. 2. As shown in FIG. 2, when the filter is stretched, the pores of the foam are more open than in FIG. 1. In FIG. 3, the filter is again curved, and faeces 104 is expelled from the pores of the foam 102 as a result of the pumping function achieved by repetitive bending (or folding) of the filter.

Figure 4A:
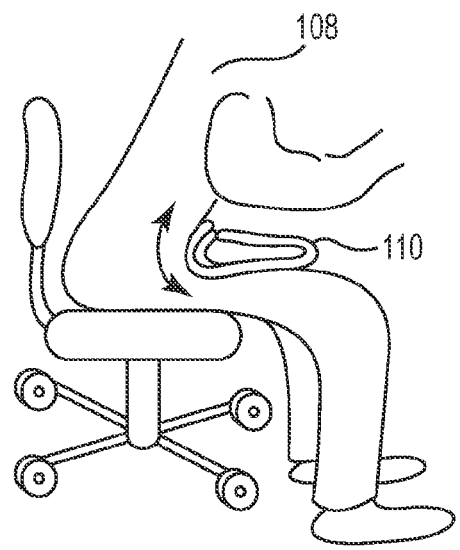
FIGS. 4A-4C and 5A-5C show different positions of a user of an ostomy system and corresponding states of the filter of the system.
Figure 4B:
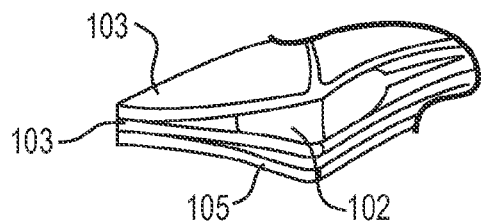
Figure 4C:
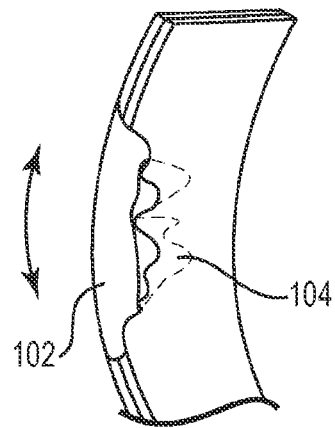
Figure 5A:
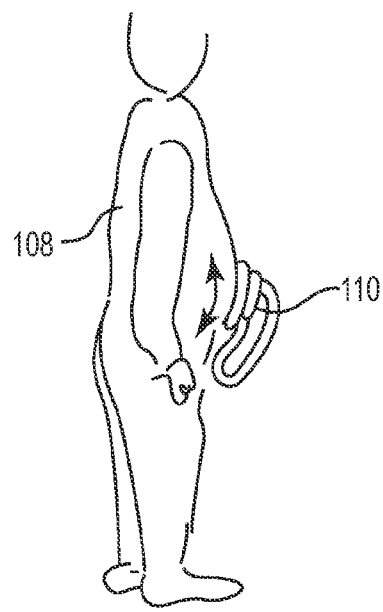
Figure 5B:
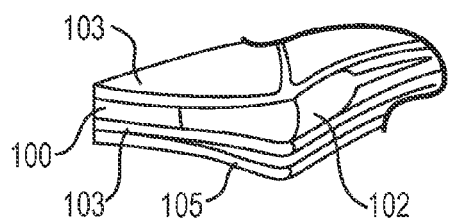
Figure 5C:
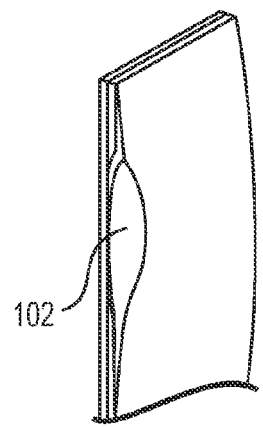

FIG. 4A illustrates a user 108 of an ostomy system 110 according to the invention, the user being seated. As shown in FIG. 4B, the foam 102 of the filter system 100 is partially compressed. As the user rises to a standing position as shown in FIG. 5A, the pores of the foam open, and as the user is seated again, faeces 104 is expelled from the foam as illustrated in FIG. 4C in the manner described above in connection with FIGS. 1-3. FIGS. 5B and 5C illustrate the state of the filter 100 corresponding to the user's positions of FIG. 5A. In FIGS. 4B and 5B a connecting sheet 105 is provided below a lower one of the sheets 103 in order to connect the filter system 100 to a flange for attaching the system to a patient's body, as described in further detail below with reference to FIGS. 7-12.

Figure 6:
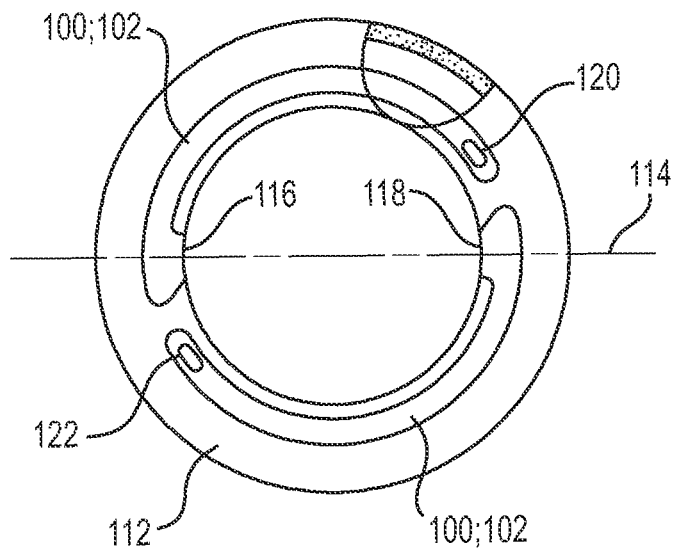
FIG. 6 shows an example of the relative position of a filter arrangement with respect to a folding line of the ostomy system with the filter arranged in a coupling system of the ostomy system.

As illustrated in FIG. 6, the filter 100 with foam 102 may form part of a coupling system 112 for securing the drainage bag of the ostomy system in relation to the user's body. In the configuration of FIG. 6, the filter arrangement comprises two filter sections, respective inlets 16 and 118 of which are intersected by a folding line 114 of the ostomy system. Accordingly, faeces is expelled from the foam 102 when the drainage bag and/or filter system folds, as described above in connection with FIGS. 1-5. The two filter sections depicted in FIG. 6 define flatus gas outlets 120 and 122, through which gas may escape to the surroundings of the drainage bag, e.g. to an outer bag or to the surrounding atmosphere.

Figure 7:
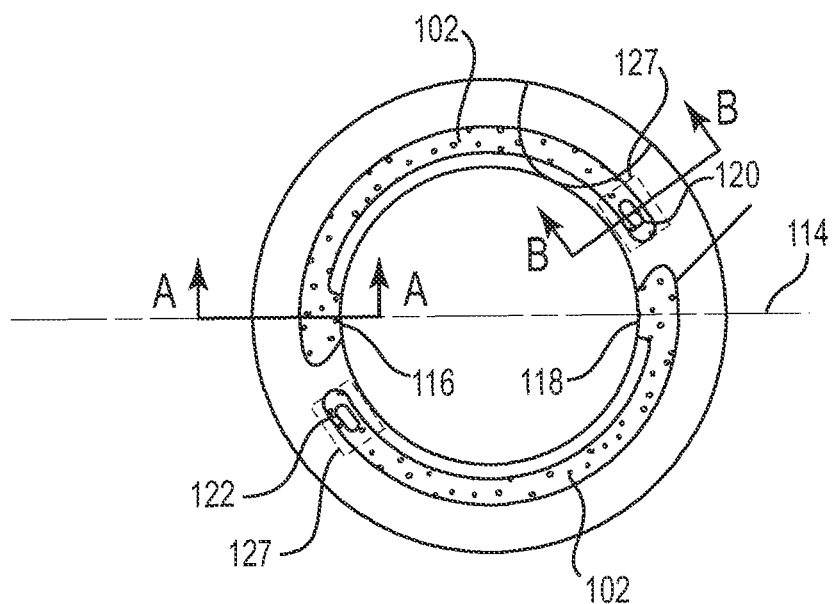
FIG. 7 shows an embodiment similar to the embodiment of FIG. 6.
Figure 8:
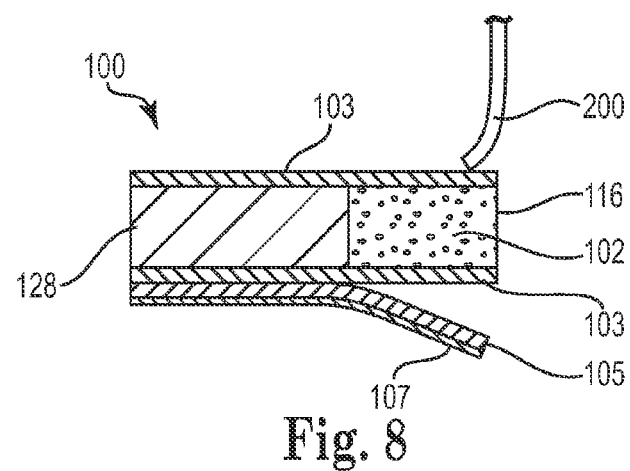
FIGS. 8 and 9 show cross sections of the embodiment of FIG. 7.
Figure 9:
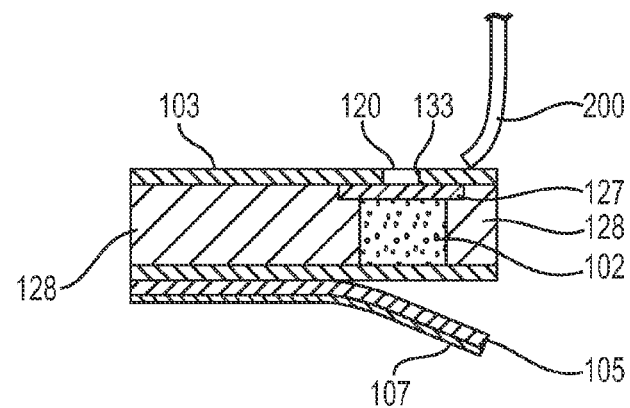
Figure 10:
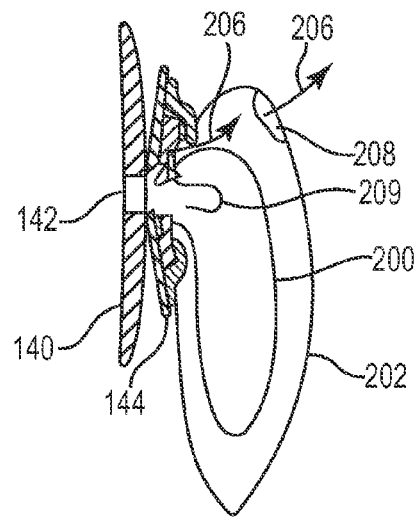
FIG. 10 illustrates the travel path of flatus gasses in an embodiment of the ostomy system of the invention.

FIG. 7 shows an embodiment similar to the embodiment of FIG. 6, in which gas permeable hydrophobic membranes 127, indicated by dashed lines, cover the flatus gas outlets 120 and 122. FIG. 8 shows a cross-sectional view along line A-A in FIG. 7. At inlet 116, the open-cell foam 102 faces the interior of inner bag (or "drainage bag") 200, which is attached to an upper one of the sheets 103. A closed-cell foam 128 is provided adjacent the open-cell foam 102 and between the sheets 103. An adhesive layer 107 covers connecting sheet 105 for attachment thereof to a supporting flange of the ostomy system as described below with reference to FIGS. 11 and 12. Within the open-cell foam 102, flatus gas and possibly liquid faeces travel from the inlet 116 to the outlet 120, cf. FIG. 7. FIG. 9 shows a cross-section through outlet 120. Between upper sheet 103 and open-cell foam 102 there is provided a gas permeable hydrophobic membrane 127, which allows flatus gas to escape from the open-cell foam 102 to the interior of outer bag 202, cf. FIG. 10. Flatus gas escape via an opening or perforation 133 provided in upper sheet 103. In FIG. 10, the travel path of flatus gas from the inner bag 200 to the interior of the outer bag 202 and from there to an exterior environment via activated carbon filter 209 is illustrated by arrows 206. FIG. 10 also illustrates that the inner bag 200 connected to the filter 100 (cf. FIGS. 8 and 9) is attached to a supporting flange 144, which is secured to a body flange 140. An opening 142 is provided for connecting the ostomy system to the patient's stoma to receive bodily waste.

Figure 11:
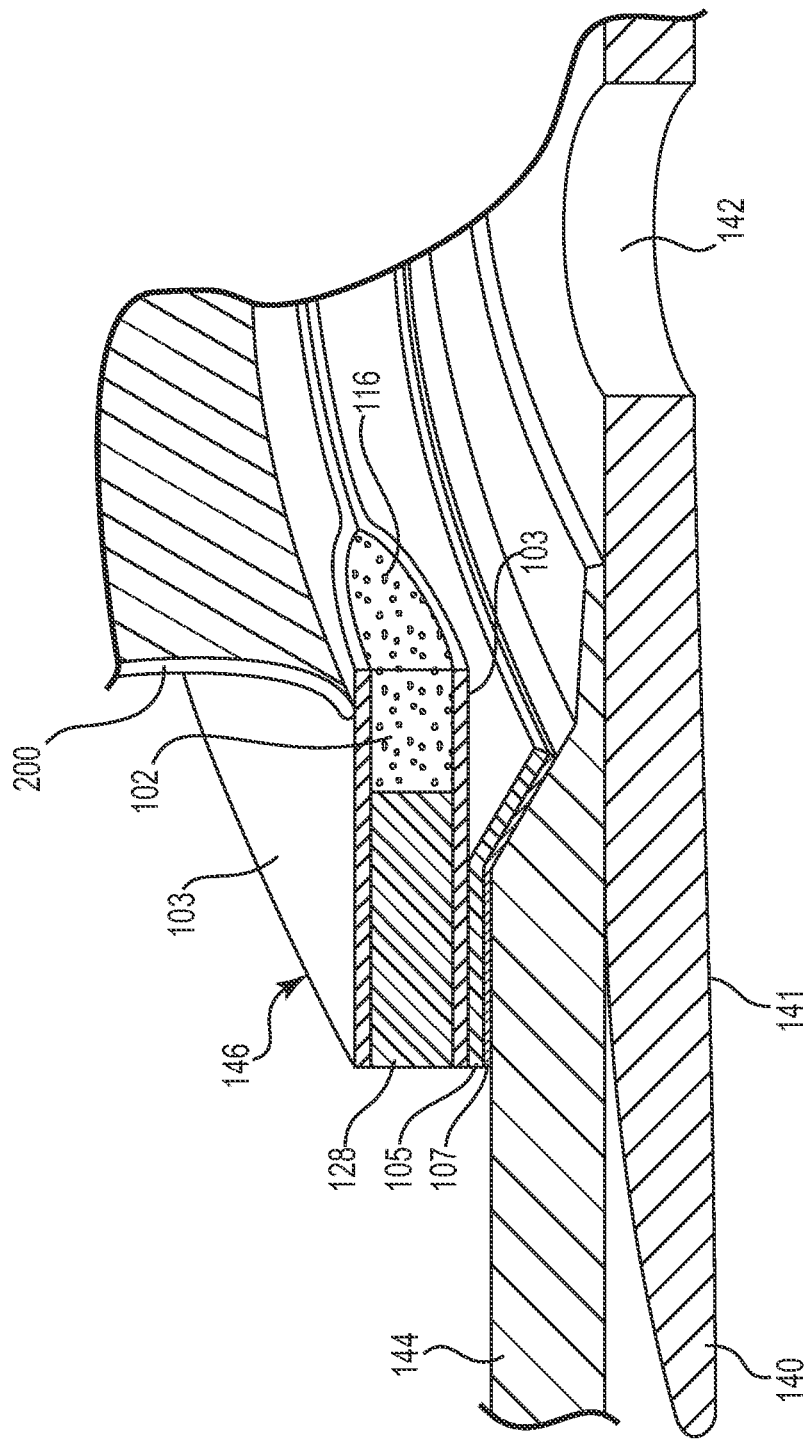
FIGS. 11 and 12 show partial cross sections in a perspective view of the embodiment of FIGS. 7-10.
Figure 12:
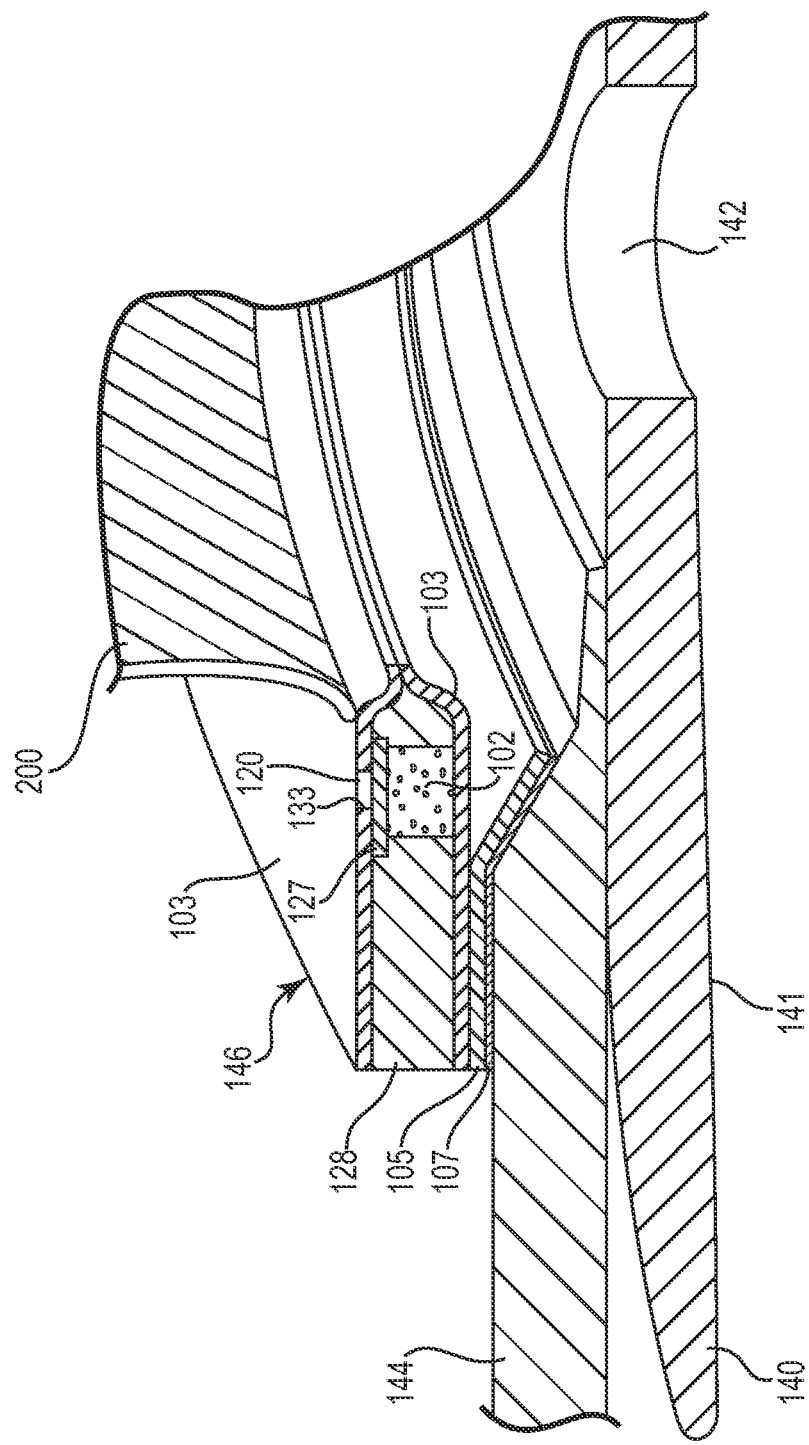

FIGS. 11 and 12 show partial cross sections in a perspective view corresponding to the views of FIGS. 8 and 9, respectively. Accordingly, FIG. 11 shows a cut through the system in the area of inlet 116, and FIG. 12 shows a cut through the system in the area of outlet 120. As illustrated in FIGS. 11 and 12, the filter system comprising open-cell foam 102, closed-cell foam 128 and sheets 103 constitutes a filter flange 146, which is attached to the supporting flange 144 via the connecting sheet 105 with the adhesive layer 107. The supporting flange 144 is in turn attached to the body flange 140, which comprises a layer 141 of hydrocolloid adhesive for attachment of the ostomy system to the patient's body. In order to reduce the risk that a displacement force applied to the inner bag 200 results in detachment of the filter flange 146 from the supporting flange 144, the line of attachment of the inner bag 200 to the filter flange 146 is radially displaced with respect to the contact area between the filter flange 146 and the supporting flange 144.

In the configuration of FIG. 13, the filter 100 does not form part of the coupling system 124, but is arranged near a border edge of the drainage bag 126. Such a configuration is useful in case the stoma of the user is located so that the folding line of the bag 126 does not intersect the coupling system. It will be appreciated that other positions of the filter 100 are feasible, and that multiple filters may be provided at different locations.

The invention claimed is:

1. An ostomy system for receiving bodily waste, comprising:
    a drainage bag;
    a coupling system configured to secure the drainage bag to a stoma of a user;
    a filter comprising a foam positioned at least at a filter inlet to prevent liquid and solid particles from passing from the drainage bag to its surroundings, the foam defining a passageway for releasing flatus gasses from the drainage bag to the surroundings;
    wherein the filter is pre-folded and has a folding line that intersects the filter inlet of the filter, and the filter is integrated with the coupling system such that the filter inlet of the filter is inside the drainage bag and folding/unfolding the filter about the folding line moves the foam to displace faeces away from the filter inlet of the filter.

2. An ostomy system according to claim 1, wherein the folding line intersects the filter at a distance from the filter inlet.

3. An ostomy system according to claim 1, wherein the filter is arranged between the coupling system and the drainage bag.

4. An ostomy system according to claim 1, wherein the drainage bag is impermeable to flatus gasses.

5. An ostomy system according to claim 3, wherein said surroundings of the drainage bag comprise an outer bag that is secured in relation to the user's body and in relation to the drainage bag by means of said coupling system.

6. An ostomy system according to claim 5, wherein the outer bag is fabricated from a material that is impermeable to flatus gasses and comprises an outlet with a flatus filter for releasing flatus gasses from the outer bag.

7. An ostomy system according to claim 1, wherein said passageway further extends through a gas permeable membrane.

8. An ostomy system according to claim 1, wherein the filter comprises a filter flange, and wherein the drainage bag is connected to a first surface of the filter flange along an attachment zone, and wherein the coupling system is connected to the filter flange along a contact area, whereby said attachment zone is radially displaced with respect to said contact area.

9. An ostomy system according to claim 1, wherein the foam is an open-cell foam, and wherein the filter comprises a filter flange, in which the open cell foam is supported by a closed-cell foam.

10. An ostomy system according to claim 1, wherein the drainage bag is of a structure which essentially maintains its physical integrity upon immersion in water.

11. An ostomy system according to claim 1, wherein the coupling system comprises means for forcing the flow of flatus gasses along a predetermined passageway.

12. An ostomy system according to claim 1, wherein the filter is closer to the coupling system than the filter is to the drainage bag.

13. A kit of parts comprising:
    an ostomy system for receiving bodily waste including:
        a drainage bag;
        a coupling system configured to secure the drainage bag to a stoma of a user;
        a filter comprising a foam positioned at least at a filter inlet of the filter to prevent liquid and solid particles from exiting the drainage bag, the foam defining a passageway for releasing flatus gasses from the drainage bag;
        wherein the filter is integrated with the coupling system such that the filter inlet of the filter is inside the drainage bag; and
    a set of instructions instructing a user how to provide the drainage bag with a folding line prior to attachment of the ostomy system to the body;

wherein folding/unfolding of the filter about the folding line is adapted to move the foam to displace faeces away from the filter inlet of the filter.

* * * * *